(12) United States Patent
Schouwenburg et al.

(10) Patent No.: US 11,822,861 B2
(45) Date of Patent: *Nov. 21, 2023

(54) SYSTEMS AND METHODS FOR CHARACTERIZING A FOOT OF AN INDIVIDUAL

(71) Applicant: Aetrex, Inc., Teaneck, NJ (US)

(72) Inventors: Kegan Leann Schouwenburg, New York, NY (US); Nathan Ghabour, Jersey City, NJ (US); Alexander Crosby, Providence, RI (US)

(73) Assignee: Aetrex, Inc., Teaneck, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/683,042

(22) Filed: Feb. 28, 2022

(65) Prior Publication Data
US 2022/0288857 A1    Sep. 15, 2022

Related U.S. Application Data

(63) Continuation of application No. 16/697,846, filed on Nov. 27, 2019, now Pat. No. 11,260,597, which is a
(Continued)

(51) Int. Cl.
| | |
|---|---|
| *G06F 30/17* | (2020.01) |
| *B29C 64/393* | (2017.01) |
| *G16B 5/00* | (2019.01) |
| *B33Y 50/00* | (2015.01) |
| *G05B 19/4099* | (2006.01) |
| *B29C 64/386* | (2017.01) |
| *G06F 30/00* | (2020.01) |

(Continued)

(52) U.S. Cl.
CPC ............ *G06F 30/17* (2020.01); *B29C 64/386* (2017.08); *B29C 64/393* (2017.08); *B33Y 50/00* (2014.12); *G05B 15/02* (2013.01); *G05B 19/4099* (2013.01); *G06F 30/00* (2020.01); *G06F 30/12* (2020.01); *G16B 5/00* (2019.02); *B33Y 10/00* (2014.12); *B33Y 30/00* (2014.12); *B33Y 50/02* (2014.12); *G05B 2219/23005* (2013.01); *G05B 2219/23011* (2013.01); *G16H 50/50* (2018.01); *Y02P 90/02* (2015.11)

(58) Field of Classification Search
CPC ......... B33Y 50/00; B33Y 50/02; B33Y 10/00; B33Y 30/00; G05B 15/02; G05B 19/40
USPC ........................................... 700/98
See application file for complete search history.

(56) References Cited

U.S. PATENT DOCUMENTS

| | | | | |
|---|---|---|---|---|
| 8,838,263 | B2 * | 9/2014 | Sivak | B33Y 80/00 |
| | | | | 700/118 |
| 9,443,353 | B2 * | 9/2016 | Vaddadi | G06T 19/20 |
| 9,486,142 | B2 * | 11/2016 | Hielscher | A61B 5/7264 |

* cited by examiner

Primary Examiner — Md Azad
(74) Attorney, Agent, or Firm — Lowenstein Sandler LLP

(57) ABSTRACT

A method for generating an orthotic device is disclosed. The method includes receiving data from a client device of a patient, the data comprising patient information and image data representative of a body part of the patient. The method further includes generating, based on the image data, three-dimensional model data representative of the body part, and generating parametric CAD model data of the orthotic device based on the three-dimensional model data and the patient information. The parametric CAD model data is transmitted to a three-dimensional printer, wherein the three-dimensional printer is to generate the orthotic device based on the parametric CAD model data.

20 Claims, 9 Drawing Sheets

Related U.S. Application Data continuation of application No. 15/894,241, filed on Feb. 12, 2018, now Pat. No. 10,496,786, which is a continuation of application No. 14/961,769, filed on Dec. 7, 2015, now Pat. No. 9,892,228, which is a continuation of application No. 14/677,894, filed on Apr. 2, 2015, now Pat. No. 9,449,141, which is a continuation of application No. 14/341,632, filed on Jul. 25, 2014, now Pat. No. 9,760,674.

(60) Provisional application No. 61/981,753, filed on Apr. 19, 2014, provisional application No. 61/858,685, filed on Jul. 26, 2013.

(51) Int. Cl.
| | |
|---|---|
| *G06F 30/12* | (2020.01) |
| *G05B 15/02* | (2006.01) |
| *G16H 50/50* | (2018.01) |
| *B33Y 50/02* | (2015.01) |
| *B33Y 10/00* | (2015.01) |
| *B33Y 30/00* | (2015.01) |

550

```
Start
  │
  ▼
Receive a plurality of user inputs at a client device, the user inputs corresponding to
patient information
                                                                              555
  │
  ▼
Generate one or more indicators to guide the capturing of image data of a body part
                                                                              560
  │
  ▼
Capture the image data of the body part
                                                                              565
  │
  ▼
Transmit the patient information and image data to a remote device for processing,
in which the remote device is to generate, based on the patient information and the
image data, three-dimensional model data representative of the body part
                                                                              570
  │
  ▼
End
```

FIG. 5B

SYSTEMS AND METHODS FOR CHARACTERIZING A FOOT OF AN INDIVIDUAL

CROSS-REFERENCE TO RELATED APPLICATIONS

This application is a continuation of U.S. Non-Provisional patent application Ser. No. 16/697,846, filed Nov. 27, 2019, which is a continuation of U.S. Non-Provisional patent application Ser. No. 15/894,241, filed Dec. 12, 2018, which is a continuation of U.S. Non-Provisional patent application Ser. No. 14/961,769, filed Dec. 7, 2015, which is a continuation of U.S. Non-Provisional patent application Ser. No. 14/677,894, filed Apr. 2, 2015, which is a continuation of U.S. Non-Provisional application Ser. No. 14/341,632, filed Jul. 25, 2014, which claims the benefit of priority of U.S. Provisional Patent Application No. 61/981,753, filed Apr. 19, 2014, and U.S. Provisional Patent Application No. 61/858,685, filed Jul. 26, 2013, all of which are hereby incorporated by reference herein in their entireties.

TECHNICAL FIELD

This disclosure relates to the field of corrective orthotic devices, in particular, to generating models from user-captured data to produce orthotic devices.

BACKGROUND

An orthotic insert is a type of orthotic device that, when inserted into a shoe and applied to a foot, supports the foot by redistributing ground reaction forces while properly aligning foot joints during motion. Orthotic inserts are typically used to treat biomechanical deformities as well as inflammatory conditions (e.g., plantar fasciitis) in patients.

Various methods have been employed to produce orthotic inserts. For example, plaster cast, gait scanning, and laser scanning methods attempt to capture plantar geometry in a weight bearing position. However, such methods are generally slow in acquiring orthotic data, are expensive, and are limited in the range of characteristics that they can provide to the resulting orthotic device. In such methods, the orthotic device is customizable insofar as it is designed with a particular ailment in mind, while the treatment is implemented as a one-size-fits-all solution that may be far from optimal for some patients.

Moreover, current methods of orthotic insert production are generally limited to the machining of hard materials (top down approaches). This also limits the range of characteristics (flexibility, shock absorption, weight, etc.) of the end product. Shapes of the orthotic inserts tend to be mixed and matched from a database, which may result in orthotic inserts that are unique to a particular lab or production facility but not to a particular patient.

SUMMARY

The following is a simplified summary of the disclosure in order to provide a basic understanding of some aspects of the disclosure. This summary is not an extensive overview of the disclosure. It is intended to neither identify key or critical elements of the disclosure, nor delineate any scope of the particular implementations of the disclosure or any scope of the claims. Its sole purpose is to present some concepts of the disclosure in a simplified form as a prelude to the more detailed description that is presented later.

In one aspect, a method includes receiving, from a client device, data related to a patient, the data including patient information and image data, in which the image data is representative of a body part of the patient. The method further includes generating, based on the image data, three-dimensional model data representative of the body part. The method further includes generating parametric computer-aided design (CAD) model data for an orthotic device based on the three-dimensional model data and the patient information. The method further includes transmitting the parametric CAD model data to a three-dimensional printer, wherein the three-dimensional printer is to generate the orthotic device based on the parametric CAD model data.

In another aspect, a method includes receiving a plurality of user inputs at a client device, the user inputs corresponding to patient information. The method further includes generating one or more indicators to guide the capturing of image data of a body part. The method further includes capturing the image data of the body part. The method further includes transmitting the patient information and image data to a remote device for processing, wherein the remote device is to generate, based on the patient information and the image data, three-dimensional model data representative of the body part.

In one or more of the disclosed implementations, computing devices for performing the operations of the above described implementations are also disclosed. Additionally, in implementations of the disclosure, a computer readable storage media stores methods for performing the operations of the above described implementations.

BRIEF DESCRIPTION OF THE DRAWINGS

The present disclosure is illustrated by way of example, and not by way of limitation, in the figures of the accompanying drawings, in which:

FIG. 5B is a flow diagram illustrating a method for capturing data from a user for use in producing an orthotic device according to an implementation of the disclosure.

DETAILED DESCRIPTION

Figure 1A:
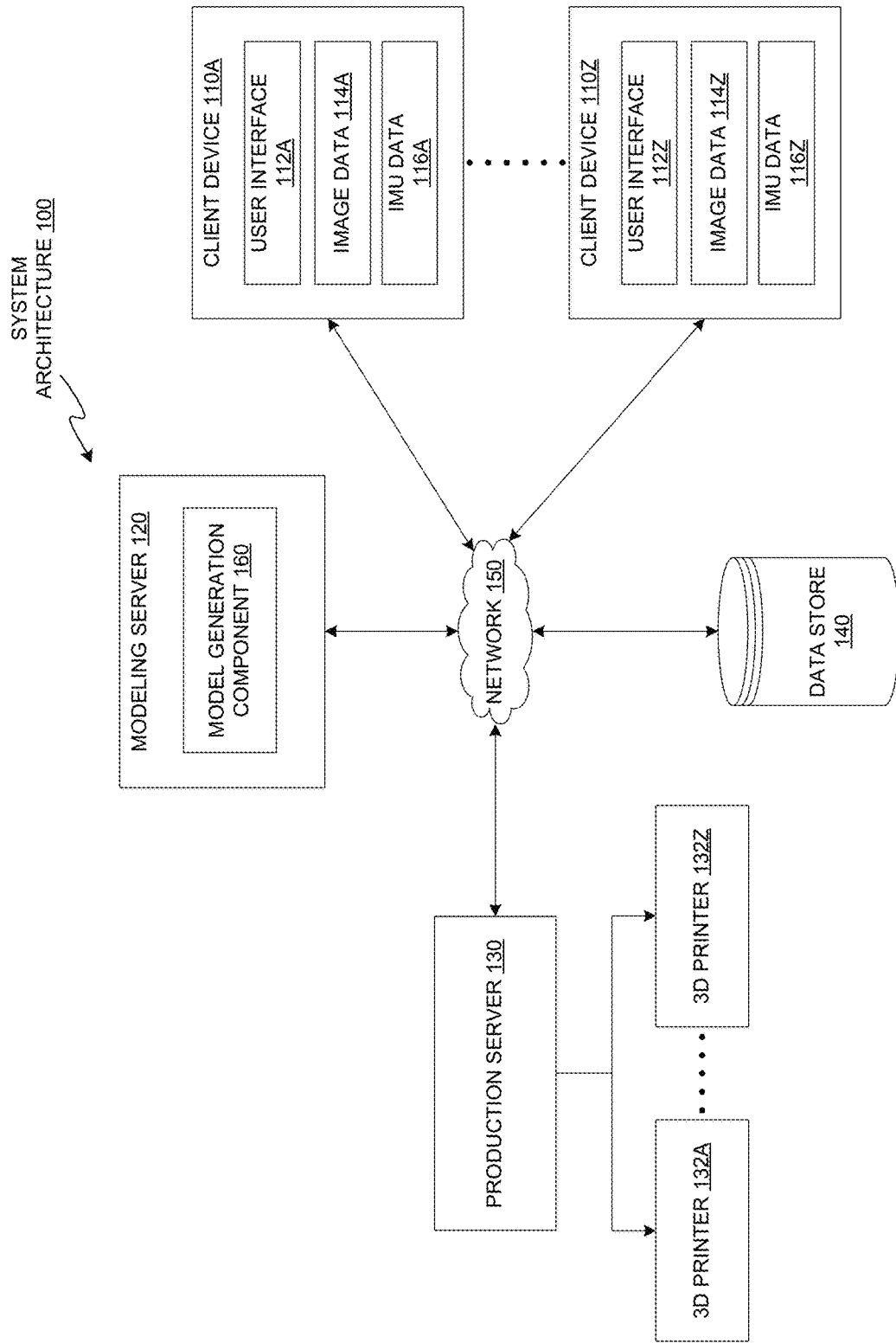
FIG. 1A illustrates an example system architecture in accordance with an implementation of the disclosure.

Implementations are described for producing orthotic devices from user-captured data. Image data of a body part of a patient (e.g., the patient's foot) can be captured using a client device, such as a mobile device having a camera. An interface implemented on the client device can instruct a user of the device (e.g., the patient, a physician, an assistant, etc.) to capture image data (e.g., images and/or video) of the body part. For example, the interface may utilize various indicators (e.g., visual cues) to guide data capture. If the device includes an inertial measurement unit (IMU), then IMU data may also be captured during the image data capture, which may facilitate downstream data processing. The device can also allow for data entry of patient information, which can include physical parameters related to the patient (e.g., height, weight, age, pre-existing medical conditions, etc.).

The captured image data, IMU data, and patient information may be transmitted to a server, which uses the received data to generate a three-dimensional (3D) model of the body part. In doing so, relevant measurements related to the body part may be extracted, and are in turn used to generate a parametric CAD model of an orthotic device (e.g., an orthotic insert). The parametric CAD model may be transmitted, for example, to a manufacturing facility that can print the orthotic device using a 3D printer.

The implementations of the present disclosure provide several advantages over traditional orthotic device technologies, and orthotic insert technologies in particular. The implementations described herein effectively transform a mobile device into a scanner that is portable, lightweight, and accurate, allowing for a patient to perform his/her own scans without requiring trained medical personnel. In addition, a digital 3D model of a foot in digital format facilitates error checking of the quality of the scan through visualization and comparison with prior scans and studies. The digital 3D model can continue to be inspected, re-used, or re-processed by the algorithm or updated based on new algorithms and/or updated patient data. Once complete, the digital 3D model can be transmitted from a patient device or a device of the physician to a manufacturing facility for production of the orthotic insert, alleviating the need to physically transport a mold or cast (which typically cannot be re-used) to the manufacturing facility. The level of accuracy and consistency in the digital 3D model of a foot, as provided by the disclosed implementations, outperforms plaster cast and gait scanning methods. Moreover, the implementations described herein can produce an orthotic insert with variable density by incorporating surface and sub-surface structures that further customize the mechanical properties of the orthotic insert, resulting in an orthotic insert that is extremely thin, cushioned, and patient-optimized all at once.

The term "orthotic device", as used herein, refers to any device worn by or externally applied to an individual that provides neuromuscular support to the individual, provides skeletal support to the individual, and/or provides prophylactic functionality. The term "corrective device", as used herein, refers to a type of orthotic device that provides a therapeutic benefit to an individual (e.g., who may be referred to herein as "a patient") when worn by or externally applied by to the individual. While the implementations herein are described with respect to orthotic devices for treating or supporting a patient's foot (i.e., orthotic shoe inserts), it is to be understood that the systems and methods described herein are applicable to the production of other types of devices. For example, the implementations described herein are generally applicable to the production of devices that are customized to fit to the human body, devices utilizing customization and optimization related to human activity, bio-mechanics, and anatomy, processes that can be applied to consumer devices with or without specialized hardware or skill, and devices that utilize components or structures that would be difficult to produce in mass quantities with traditional manufacturing approaches. Such devices may include, but are not limited to, helmets, body armor, sports equipment, prosthetics, casts, splints, clothing, furniture, vehicle seats, vehicle or robotic control mechanisms, physical therapy devices, gloves, surgical instruments, and sterile medical packing.

FIG. 1A illustrates an example system architecture 100, in accordance with an implementation of the disclosure, for generating an orthotic device. The system architecture 100 includes client devices 110A-110Z, a modeling server 120, a production server 130, 3D printers 132A-132Z, a data store 140, and a network 150.

In one implementation, the client devices 110A-110Z may each include computing devices such as personal computers (PCs), laptops, mobile phones, smart phones, tablet computers, netbook computers etc. Client devices 110A-110Z may also be referred to as "user devices". An individual user may be associated with (e.g., own and/or use) one or more client devices (e.g., one or more of client devices 110A-110Z). Client devices 110A-110Z may each be owned and utilized by different users at different locations. As used herein, a "user" may refer generally to an individual operator of one or more of client devices 110A-110Z, and may be a patient for which an orthotic device is to be produced, a clinician or physician who may be involved in the preparation of the orthotic device in conjunction with, or on behalf of, the patient, an assistant to the patient, etc.

The client devices 110A-110Z may each implement user interfaces 112A-112Z, respectively. Each of user interfaces 112A-112Z may allow a user of the respective client device 110A-110Z to send and receive information to one or more of the modeling server 120 and the production server 130. For example, one or more of the user interfaces 112A-112Z may be a web browser interface that can access, retrieve, present, and/or navigate content (e.g., web pages such as Hyper Text Markup Language (HTML) pages) provided by the modeling server 120. In one implementation, one or more of the user interfaces 112A-112Z may be a standalone application (e.g., a mobile app), which may have been provided by the modeling server 120 (e.g., as a downloadable application), that allows a user of a respective client device 110A-110Z to send and receive information to the modeling server 120. In one implementation, the user interfaces 112A-112Z guide their respective users in capturing image data of a body part, which is utilized downstream by the modeling server 120 to generate a 3D model of the body part. The term "image data" is intended to include any type of visual data that can be captured by an optical instrument (e.g., a photographic camera, a charge-coupled device (CCD) camera, an infrared camera, etc.), including videos, static images, and video frames.

In one implementation, one or more of the client devices 110A-110Z may capture and store image data 114A-114Z, respectively, which may include one or more static images, videos, and/or audio data (e.g., which may be embedded within the video data or may be a separate audio track). The image data 114A-114Z may be made accessible to other devices of the system architecture 100 via the network 150. For example, captured image data may be transmitted to (e.g., streamed in real-time during capture or transmitted at a later time after capturing the data) the modeling server 120 and/or the data store 140. Each of client devices 110A-110Z may also capture IMU data 116A-116Z, respectively, which may include gyroscopic data, magnetometer data, GPS data, etc., captured by the respective client device while in use. For example, IMU data 116A captured while a user is operating the client device 110A to capture image data 114A of his/her foot may be used to estimate the orientation of the client device 110A (e.g., if the client device is a mobile device with a camera), and may later be leveraged to identify frames of video that best capture the foot to facilitate downstream data processing. The IMU data 116A-116Z may be made accessible to other devices of the system architecture 100 via the network 150.

In one implementation, the modeling server 120 may be one or more computing devices (such as a rackmount server, a router computer, a server computer, a personal computer, a mainframe computer, a laptop computer, a tablet computer, a desktop computer, etc.), data stores (e.g., hard disks, memories, databases), networks, software components, and/or hardware components. The modeling server 120 may include a model generation component 160 (which may be executed by a processing device of the modeling server 120) that is capable of generating three-dimensional (3D) models of a patient's body part (e.g., the patient's foot) based on image data-captured by the patient/user of one of client devices 110A-110Z, as well as additional patient-related data (e.g., medical data). The model generation component 160 may also be capable of generating a parametric CAD model of an orthotic device based on the 3D model of the patient's body part. In some implementations, the model generation component 160 may be implemented on a different device than modeling server 120. For example, in some implementations, one or more of client devices 110A-110Z may implement the model generation component 160, and modeling server 120 may be omitted from the system architecture 100. In other implementations, the modeling server 120 may be combined with the production server 130 as a single server. In one implementation, the modeling server 120 may utilize high performance computing resources (e.g., available via the Internet) by outsourcing data processing functions to high-performance computing devices.

In one implementation, the production server 130 may be one or more computing devices (such as a rackmount server, a router computer, a server computer, a personal computer, a mainframe computer, a laptop computer, a tablet computer, a desktop computer, etc.), data stores (e.g., hard disks, memories, databases), networks, software components, and/or hardware components. The production server 130 may receive parametric CAD models data from the modeling server 120 via the network 150. The parametric CAD model data may be converted, by the production server 130, into a format suitable for 3D printing prior to transmitting the data to one or more of the 3D printers 132A-132Z.

In one implementation, the 3D printers 132A-132Z are communicatively coupled to the production server 130, as illustrated. In some implementations, one or more of the 3D printers 132A-132Z may be coupled to one or more of the devices of the system architecture 100 in addition to the production server 130, which may be communicatively coupled to these devices via the network 150. Each of the 3D printers 132A-132Z may be capable of one or more of fused deposition modeling, stereolithography, selective laser sintering, or any type of 3D printing technology as would be understood by one of ordinary skill in the art.

In one implementation, the data store 140 may be a memory (e.g., random access memory), a cache, a drive (e.g., a hard drive), a flash drive, a database system, or another type of component or device capable of storing data. The data store 140 may also include multiple storage components (e.g., multiple drives or multiple databases) that may also span multiple computing devices (e.g., multiple server computers), and may be cloud-based. In some implementations, the data store 140 may be a part of the modeling server 120. In some implementations, the data store 140 may be distributed among and accessible to one or more of the client devices 110A-110Z, the modeling server 120, and the production server 130. One or more of the devices of the system architecture 100 may utilize the data store 140 to store public and private data, and the data store 140 may be configured to provide secure storage for private data (e.g., patient-specific information).

In one implementation, the network 150 may include a public network (e.g., the Internet), a private network (e.g., a local area network (LAN) or wide area network (WAN)), a wired network (e.g., Ethernet network), a wireless network (e.g., an 802.11 network or a Wi-Fi network), a cellular network (e.g., a Long Term Evolution (LTE) network), routers, hubs, switches, server computers, or a combination thereof. In some implementations, the network 150 may be a combination of different types of networks. Image data 114A-114Z and IMU data 116A-116Z of any of client devices 110A-110Z may be transmitted to modeling server 120 and/or production server 130 via the network 150. Likewise, 3D model data and parametric CAD model data may be transmitted from the modeling server 120 to any one of the client devices 110A-110Z and the production server 130 via the network 150.

Figure 1B:
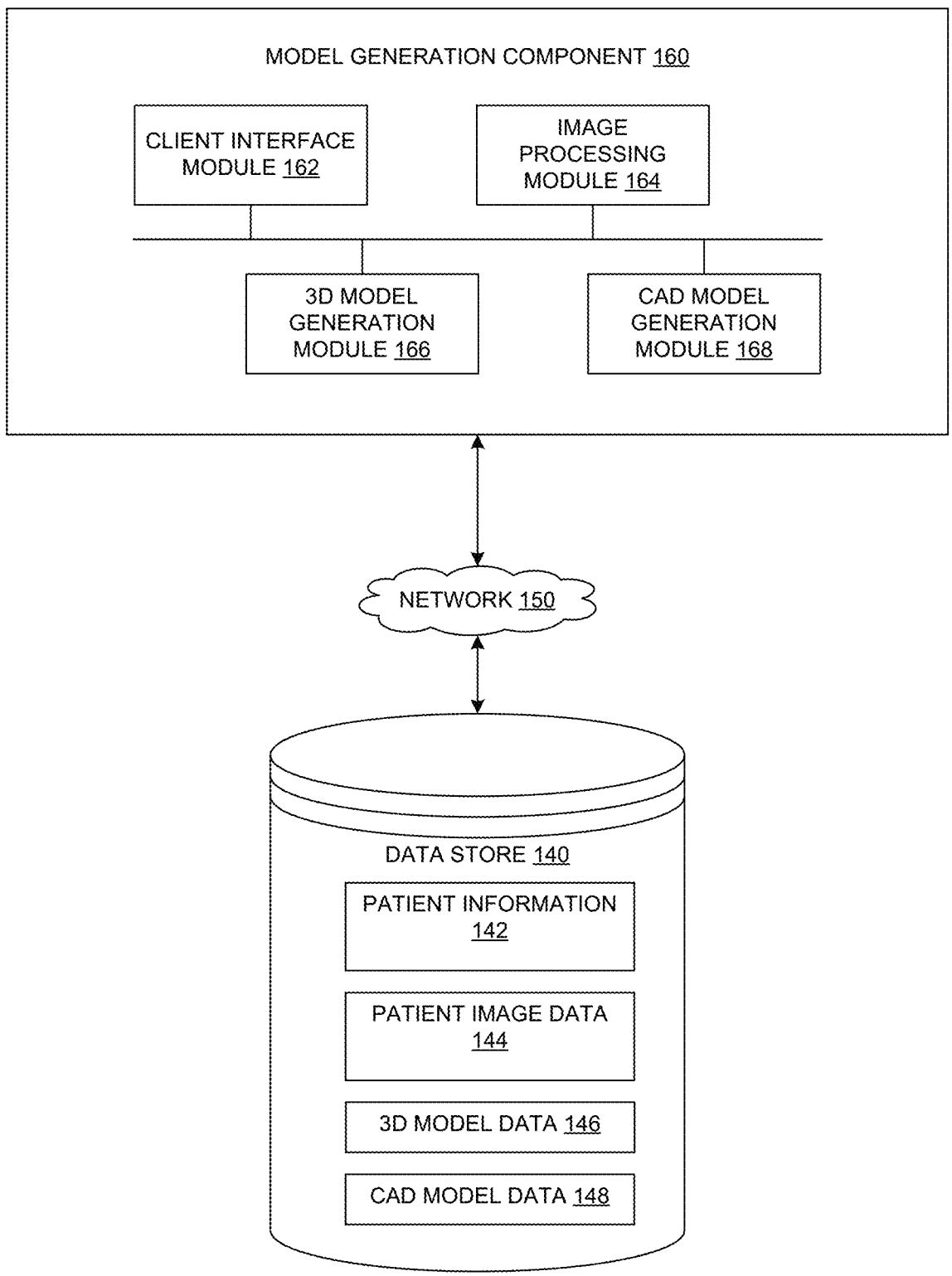
FIG. 1B is a block diagram illustrating features of a model generation component in accordance with an implementation of the disclosure.

FIG. 1B is a block diagram illustrating features of a model generation component 160 in accordance with an implementation of the disclosure. The model generation component 160 may be the same as its identically named counterpart of FIG. 1A. In one implementation, the model generation component 160 includes a client interface module 162, an image processing module 164, a 3D model generation module 166, and a CAD model generation module 168. More or less components may be included in the model generation component 160 without loss of generality. For example, two or more of the modules may be combined into a single module, or one of the modules may be divided into two or more modules. In one implementation, one or more of the modules may reside on different computing devices (e.g., different server computers, on a client device, distributed among multiple client devices, etc.). The model generation component 160 was described as being implemented by the modeling server 120 of FIG. 1A, but may be implemented by any of the client devices 110A-110Z and the production server 130. For example, a client device (e.g., client device 110A) may be programmed to perform some or all of the functions of the model generation component 160. When the model generation component 160 is implemented on a client device, any functions described with respect to the model generation component 160 that "receive", "transmit", "generate", "retrieve", "identify", "determine", "select", etc., are understood to refer to functions performed by sub-systems or sub-modules within the client device rather than across a network (e.g., the network 150), as would be appreciated by one of ordinary skill in the art.

In one implementation, the model generation component 160 is communicatively coupled to the data store 140. For example, the model generation component 160 may be coupled to the data store 140 via a network (e.g., via network 150). As described with respect to FIG. 1A, the data store 140 may be a memory (e.g., a random access memory), a cache, a drive (e.g., a hard drive), a flash drive, a database system, or another type of component or device capable of storing data. The data store 106 may also include multiple storage components (e.g., multiple drives or multiple databases) that may also span multiple computing devices (e.g., multiple server computers), and may be cloud-based. In one implementation, the data store 140 may include patient information 142, patient image data 144, 3D model data 146, and CAD model data 148. While data store 140 is illustrated and described with respect to a single patient, and it is to be understood that data store 140 may store data associated with multiple patients, and the implementations described herein may be performed for multiple patients concurrently.

The term "patient information", as used herein, refers to any alphanumeric data that may describe one or more physical aspects of a patient. The patient information 142 may include, but is not limited to, the patient's height, weight, age, ethnicity, a pre-existing medical condition (e.g., a podiatric medical condition), a measured foot length, shoe size, etc. In some implementations, the patient information is provided by the patient (e.g., using one of the client devices 110A-110Z). For example, prior to being prompted to capture image data or after capturing image data, the user may be provided with a user interface, such as a fillable-form interface, that allows the user to enter physiological and/or medical data associated with the patient (e.g., the user may be the patient, a physician of the patient, or an assistant of the patient or physician). The data may then be transmitted to the modeling server (e.g., modeling server 120) for processing. In some implementations, the patient information may be provided by a physician (e.g., using one of client devices 110A-110Z and/or using modeling server 120). In some implementations, both the patient and the physician may provide portions of the patient information. In some implementations, some or all of the information may have been previously stored in the data store. In some implementations, the patient information may be provided by more than one client device (e.g., provided by more than one of client devices 110A-110Z).

In one implementation, the patient image data 144 includes images and/or video captured by a user of a client device (e.g., one or more of client devices 110A-110Z). The patient image data 144 may also include IMU data stored along with the images and/or video (and may be time-synchronized with video frames), which may be used by the model generation component 160 during image processing.

In one implementation, the model generation component 160 utilizes the client interface module 162 to send/receive information to/from a client device. The client interface module 162 may provide an interface for requesting information from the client device. At the user end, a user interface (e.g., user interface 112A) may be in the form of a web page or a standalone application that may provide an interface to enter patient information, as well as instructions to the user as to how to capture the image data related to a body part of the patient.

Figure 2A:
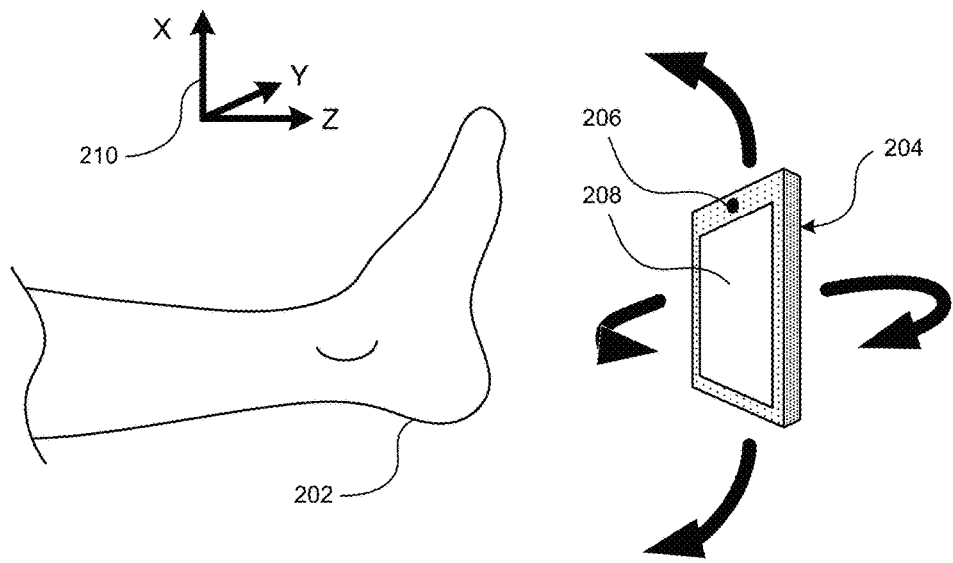
FIG. 2A illustrate the capture of image data according to an implementation of the disclosure.

In one implementation, as illustrated in FIG. 2A, a user may orient a client device 204 (which may correspond to any of client devices 110A-110Z) to capture images and/or video of a foot 202 of the patient based in accordance with instructions/indicators provided on a display 208 of the client device 204 (e.g., a visual cue). In one implementation, the instructions/indicators may alternatively or additionally include audio cues and/or haptic feedback (e.g., a vibration to indicate proper orientation of the client device 204 with respect to the foot 202). A relative coordinate axis 210 may be defined which may serve as a reference point for captured IMU data. As an illustrative implementation, a user captures video of the foot 202 at different orientations with respect to the client device 204 and takes two or more still images of the weight bearing heel and arch. The video and/or images may be captured using a built-in camera 206 of the client device 204.

Figure 2B:
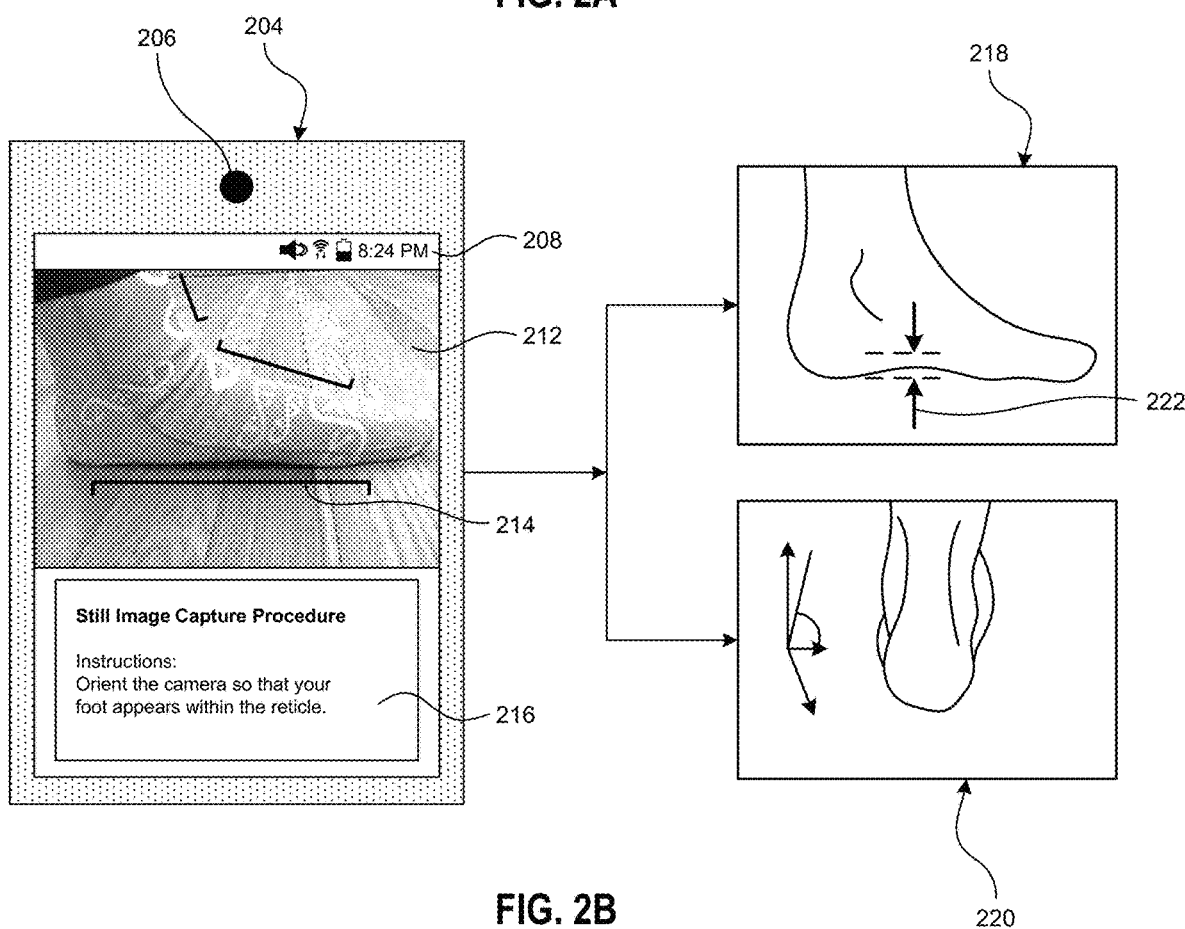
FIG. 2B illustrates the capture of image data according to another implementation of the disclosure.

As illustrated in FIG. 2B, indicators (e.g., visual cues) may be generated for display within an image window 212 within display 208 as the client device 204 is capturing image data of the foot 202. The indicators, such as reticles 214, may serve as indicators for guiding the user to capture relevant regions of the foot in weight-bearing and non-weight-bearing positions. In one implementation, indicators may include overlaid grids, horizontal lines, vertical lines, and foot-shaped targets/overlays. As the user orients the built-in camera 206 and captures image data, the client device 204 may provide additional indicators, such as instructions 216, to inform the user of his/her progress and next steps. In one implementation, visual, audio, and/or haptic cues may indicate successful progress or problems with the capture process. For example, IMU data may be used by the client device 204 to determine that the camera motion has exceeded a threshold translational or angular speed and/or acceleration, and a warning indication may be generated indicating the data captured is potentially unreliable and/or that the data should be recaptured. In some implementations, visual indicators may change shape as video is captured in order to guide the user through particularly helpful views of the foot 202. For example, such visual indicators may include arrows that direct the user. Examples of successful views may be generated for display as a result of successful capture or to provide suggested orientations to the user. For example, side view 218 and back view 220 may be generated for display as examples. Side view 218 and back view 220 may also correspond to a 3D model of the foot generated by the model generation component 160, which may have computed model data and relevant measurements 222 and transmitted the relevant data back to the client device for display. In one implementation, the client device may generate a 3D model of the foot in real-time (e.g., when the model generation component 160 is implemented on the client device).

Referring back to FIG. 1B, in one implementation, the model generation component 160 utilizes the image processing module 164. Individual frames may be selected from the video based on image quality (e.g. focus) and IMU data (if available) in order to best represent the multitude of viewing angles contained in the video. In one implementation, relative position, translational speed, and angular speed of a camera of the client device captured by the IMU of the client device. The data captured by the IMU may be used by the image processing module 164 to determine the uniqueness of information from a given video frame from other video frames based on respective positions/orientations of the other frames, which may be used to save processing time by eliminating video frames that contain redundant data. In addition, the speed of the client device may serve as an indicator of when motion artifacts (e.g., motion blur from rolling shutter cameras) are likely to be present, thus allowing frames captured during periods of fast camera movement to be eliminated.

Figure 3:
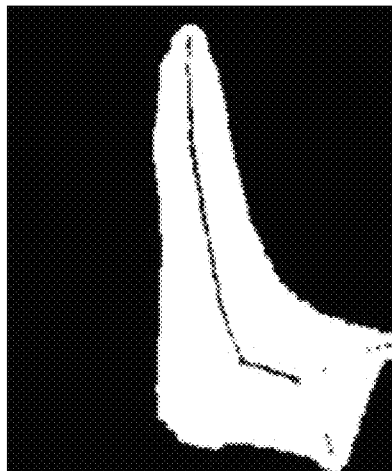
FIG. 3 illustrates image processing for model generation according to an implementation of the disclosure.
Figure 3:
Figure 3:
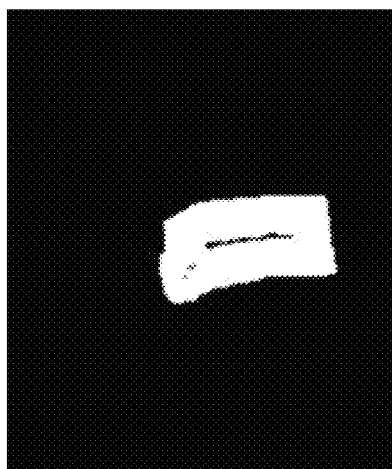
Figure 3:

In one implementation, once the frames are selected, each of the selected frames are filtered to remove background objects based on, for example, colors appearing in the frame, leaving the foot behind in the images, as illustrated in FIG. 3. In some implementations, a special colored and/or patterned sock may be worn by the patient during image data capture to isolate the foot from background objects in the video frames and still images. The pattern may be designed to aid in point finding, matching, and 3D reconstruction.

Example patterns include a randomized set of symbols in size, orientation, and color. In general, the pattern may be chosen such that its visual detail is robust against aberrations that may occur due to the camera/lens components and lighting conditions. In some implementations, 3D reconstruction may be performed with foot images without an article worn by the patient (e.g., based on skin tone, subsurface scattering effects, etc.).

In one implementation, the model generation component 160 utilizes the 3D model generation module 166 to generate 3D model data describing the body part (e.g., a 3D reconstruction of the body part). In one implementation, the frames selected by the image processing module 164 are used as inputs into an algorithm that performs registration between each frame using unique "key-points", or identifiable groups of pixels in the images. The algorithm may be a multi-view 3D reconstruction algorithm, a structure-from-motion algorithm, or another suitable algorithm. The relative location of the camera for each frame and the identified key-points can be combined to identify the locations of the key-points in 3D space as a point cloud representing an outer surface of the foot. From this approach, the plantar surface geometry can be obtained. In some implementations, a similar approach may be applied to other body parts for the purposes of obtaining 3D geometry, including, but not limited to other orthotic devices, prosthetics, and organs. In some implementations, the approach may be applied to inanimate objects (e.g., medical tools) rather than to body parts.

For certain orientations of the foot, the 3D point cloud data representing the surface of the foot, normal vectors of the points, and the IMU data combined with successive calculations and transformations of a 3D object-oriented bounding box may be used. The point cloud model may also be converted into a "solid" model of the foot for visualization purposes. The 3D model provides the capability to visualize the foot in situations, for example, when it is difficult or impractical to obtain a physical model of the foot.

In one implementation, the 3D model generation module 166 and the image processing module 164 may derive various measurements from the 3D model and selected images. The measurements include, but are not limited to, foot length, weight bearing arch height (e.g., maximum weight bearing height of the plantar arch at the arch location, weight bearing subtalar joint angle, total adjusted arch height, arch location (e.g., max plantar arch height location in sagittal and transverse planes in a neutral pose), arch width (e.g., midfoot width, width at peak arch), arch angle, prescription arch height, ball location (e.g., sesamoid location along the sagittal plane), mid heel location (e.g., mid calcaneus location along the sagittal plane), ball width (e.g., maximum forefoot width), and heel width (e.g., maximum plantar calcaneus foot width). The selected images used to perform these derivations may include, but are not limited to, an image of a heel of the foot in the frontal plane, and an image of a medial arch of the foot in the sagittal plane under weight bearing conditions.

In one implementation, one or more of measured foot length (which may have been physically measured and entered as part of the patient information), IMU data, or reference symbols on the sock (e.g., patterns or objects attached to a sock), or objects located in the environment of the foot may be used to scale the data appropriately to ensure the accuracy of the derived measurements. In one implementation, a known shoe size of the patient may be used to determine the foot length. For example, foot length, $L_M$ and $L_F$, for male feet and female feet, respectively, may be determined by:

$$L_M = 0.82387415 * S_M + 18.7012954 \qquad \text{Eq. 1}$$

$$L_F = 0.83529411 * S_F + 17.5176470 \qquad \text{Eq. 2}$$

where $S_M$ and $S_F$ are male and female shoe sizes, respectively.

In some implementations, additional parameters may be defined according to:

$$\text{arch angle} = \tan^{-1}\left(\frac{\text{arch height}}{\text{arch width}}\right), \qquad \text{Eq. 3}$$

prescription arch height=arch width*tan(arch angle+subtalar angle). Eq. 4 In one implementation, the maximum arch height may be defined to account for limitations imposed by the maximum angle that can be made between the arch length and the arch height. The max angle may be determined by the patient's forefront flexibility, according to:

$$\text{maximum arch height} = \frac{\text{arch length}}{2} * \tan(0.45 + \alpha), \qquad \text{Eq. 5}$$

where $\alpha=0$ for a rigid foot (maximum angle is 0.45 radians), $\alpha=0.05$ for a semi-rigid foot (maximum angle is 0.50 radians), and $\alpha=0.1$ for a flexible foot (maximum angle is 0.55 radians). In one implementation, if the prescription arch height is greater than the maximum arch height, the arch height will be modeled as the maximum arch height. Otherwise, the arch height will be modeled as the prescription arch height. In one implementation, if an original arch height is greater than the modeled arch height, the modeled arch height may be set as the original arch height so as to ensure that the orthotic device closely follows the contours of the foot.

In one implementation, ball width (in millimeters) is determined according to:

$$\text{narrow ball width} = 0.2224(\text{Foot Length}) + 1.0567, \qquad \text{Eq. 6}$$

$$\text{medium ball width} = 0.2335(\text{Foot Length}) + 1.1189, \qquad \text{Eq. 7}$$

$$\text{wide ball width} = 0.2380(\text{Foot Length}) + 1.1403, \qquad \text{Eq. 8}$$

for males, and:

$$\text{narrow ball width} = 0.2707(\text{Foot Length}) + 5.7137, \qquad \text{Eq. 9}$$

$$\text{medium ball width} = 0.2853(\text{Foot Length}) + 6.0209, \qquad \text{Eq. 10}$$

$$\text{wide ball width} = 0.2911(\text{Foot Length}) + 6.1437, \qquad \text{Eq. 11}$$

for females. In some implementations, the ball width may be limited based on a particular shoe for which the orthotic insert is designed to fit.

In one implementation, heel width (in centimeters) is determined according to:

$$\text{heel width} = 0.1473(\text{Foot Length}) + 2.3882. \qquad \text{Eq. 12}$$

In one implementation, arch width may be limited according to:

$$\text{heel width} \leq \text{arch width} \leq \text{ball width}, \qquad \text{Eq. 13}$$

where the arch width is constrained by these limits after all other constraints are applied to the arch width.

In one implementation, arch thickness may be determined based on a range of the patient's weight. For example, if the patient's weight in pounds is less than 140 pounds, then the arch thickness is modeled as 2 millimeters. If the patient's weight is greater than or equal to 140 pounds and less than 180 pounds, the arch thickness is modeled as 3 millimeters. If the patient's weight is greater than or equal to 180 pounds, the arch thickness is modeled as 4 millimeters.

In one implementation, the model generation component 160 utilizes the CAD model generation module 168 to generate parametric CAD model data for the orthotic device. The CAD model generation module 168 may use various algorithms to determine optimal shapes and mechanical properties of the orthotic device, which are described by the parametric CAD model data. While the parametric CAD model data may be generated based on the 3D model data representing the foot, the data may describe an orthotic insert that is designed to biomechanically adjust and support the foot rather than match the surfaces of the foot from the 3D model. The parametric CAD model data may include information such as, but not limited to, lattice designs and layouts, mesh perforation properties (e.g., hole size/shapes, pitch, etc.), curve locations, variations in lattice density, variable thicknesses, etc. In one implementation, the 3D model data and patient information (e.g., age, height, weight, medical diagnosis, etc.) may be used as inputs to a parametric CAD model of the SOL in order to output a customized model in a format suitable for 3D printing on a 3D printer. It is noted that 3D printing is illustrative, and any suitable manufacturing method may be utilized to produce the orthotic device.

Figure 4A:
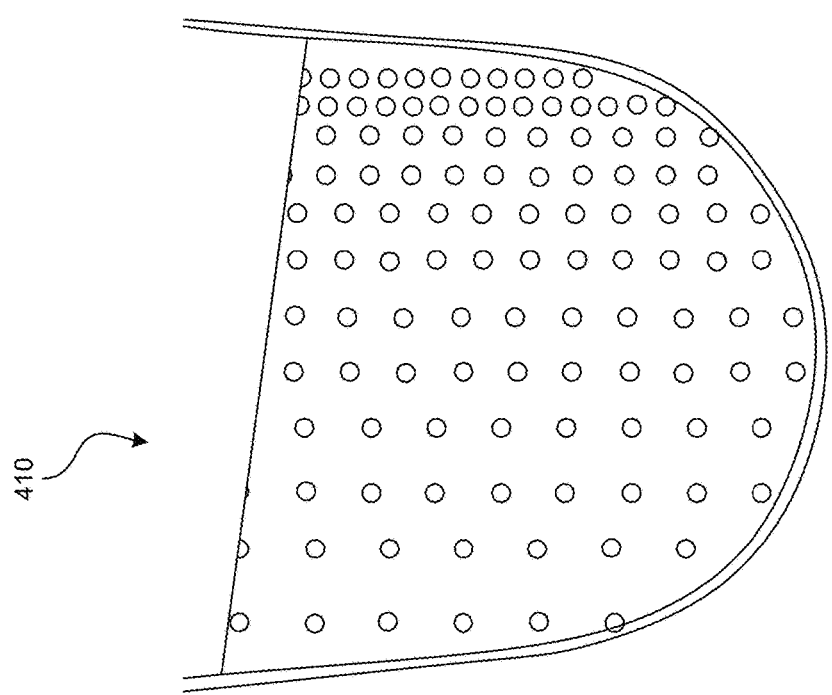
FIG. 4A is an illustration of a density lattice used in generating an orthotic insert according to an implementation of the disclosure.
Figure 4A:
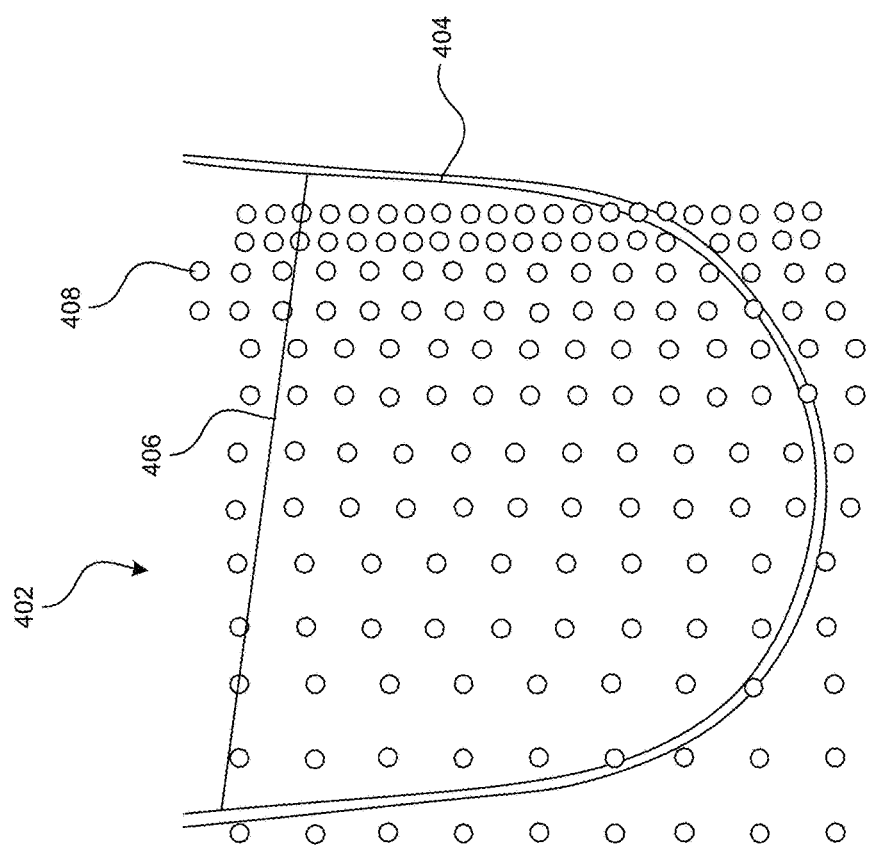
Figure 4B:
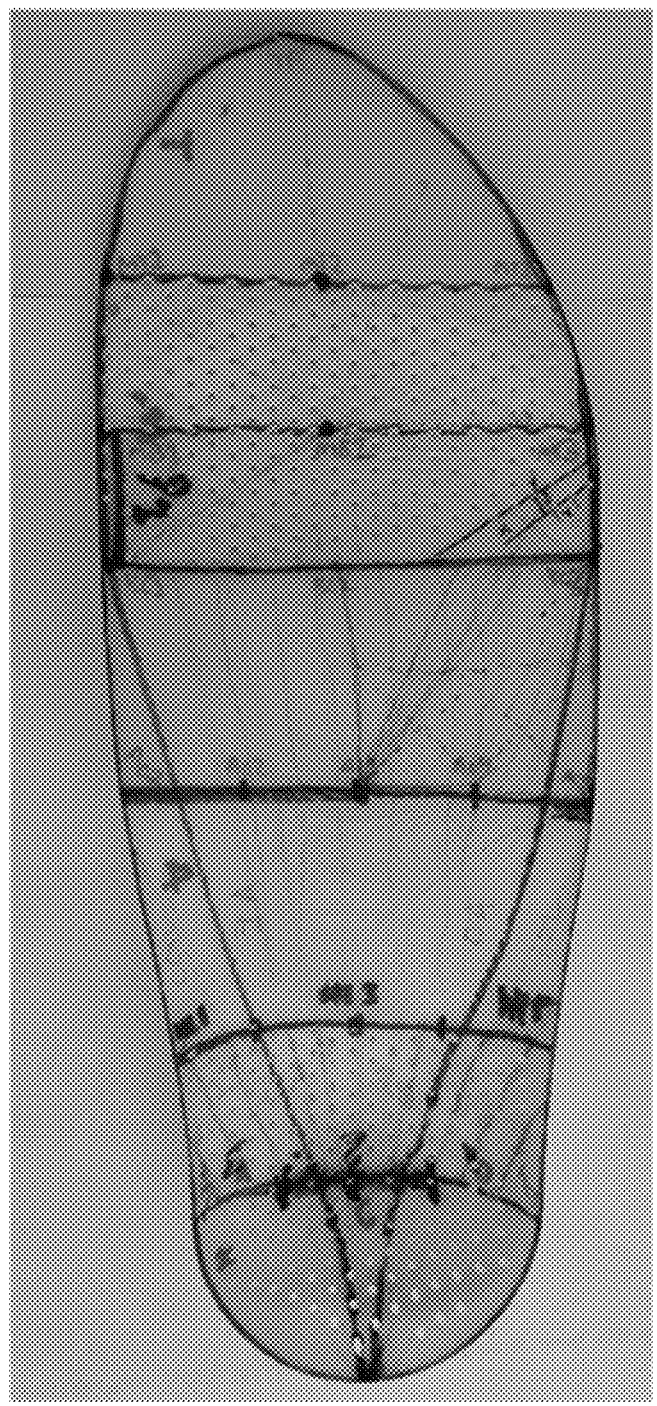
FIG. 4B shows an orthotic insert produced according to an implementation of the disclosure.

In one implementation, the CAD model generation module 168 generates a series of surfaces that may be combined to form top, bottom, and interior surfaces of a solid model of the orthotic insert, as described by the parametric CAD model data. In addition, lattice and mesh structures can be generated to define the shape and density profile of the orthotic insert, which can be placed within target treatment zones (based on the derived measurements and patient information). As illustrated in FIG. 4A, a heel portion 402 of the parametric CAD model data is depicted, including an outer boundary 404, a treatment boundary 406, and density profile 408 (represented as an array of circles that may correspond to perforations in the final orthotic insert). The treatment boundary 406 and the outer boundary 404 may define a treatment zone specific for the patient's heel. The density profile 408 may be applied to the treatment zone to provide greater material density/stiffness at the left side of the heel than the right side. A mapped heel portion 410 shows a result of the mapping after it has been applied to the treatment zone. An example of a 3D printed orthotic insert is shown in FIG. 4B, which is labeled to show relevant measurements taken into account during generation of the parametric CAD model data.

In one implementation, a heel stiffness is defined as:

$$k = 32.6 d_{diam} - 6.4 d_{space} + 95.5 d_{shell} - 13.4, \quad \text{Eq. 13}$$

where k is the stiffness (in kN/m),
$d_{diam}$ is a perforation diameter (in mm),
$d_{space}$ is a spacing between perforations (in mm), and
$d_{shell}$ is a shell size (in mm).

It is noted that the preceding equations are illustrative examples of calculations used to identify measurements for producing an orthotic insert. Other equations may also be used, and the present implementations are not limited to the preceding examples.

Figure 5A:
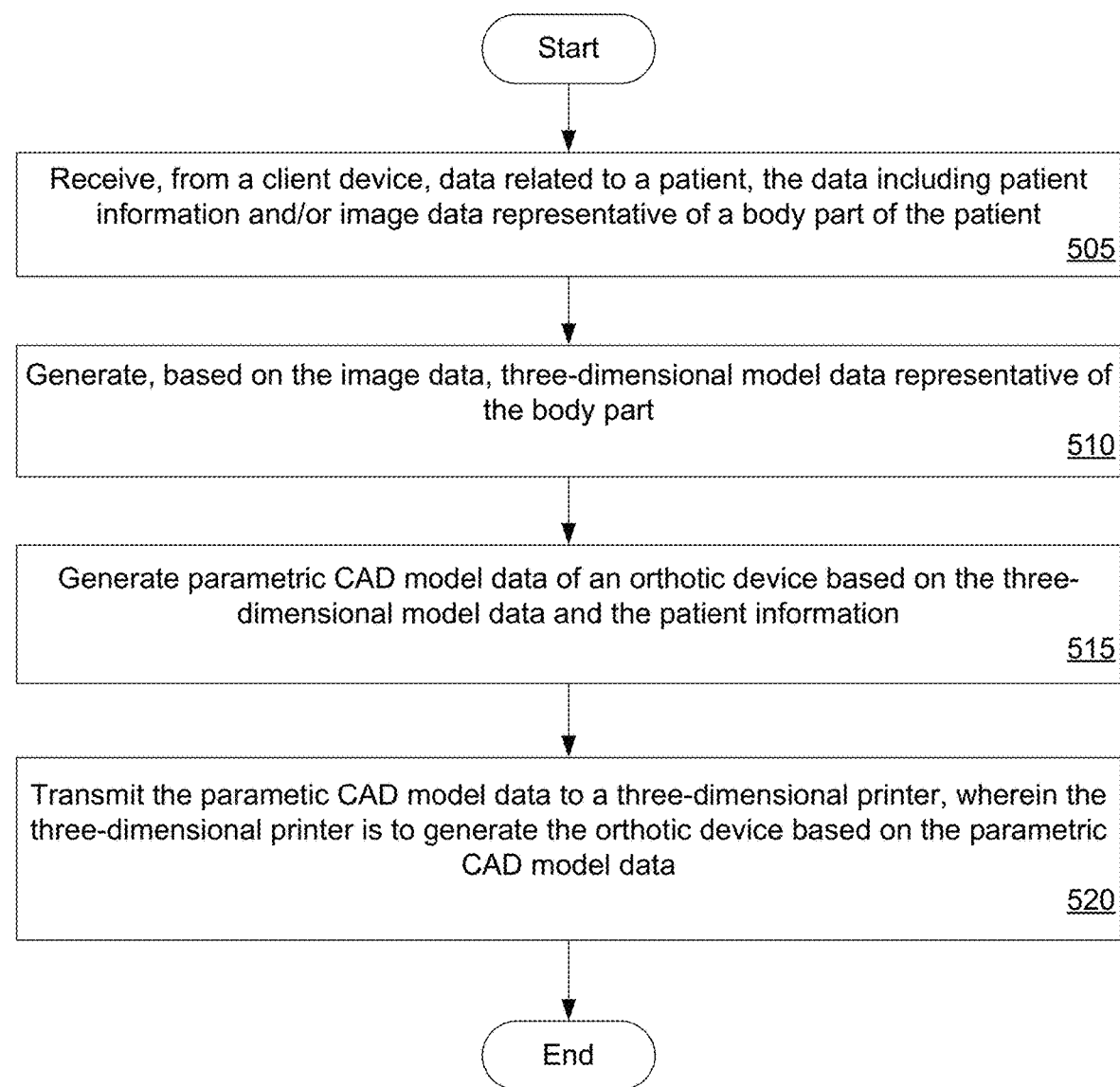
FIG. 5A is a flow diagram illustrating a method for producing an orthotic device according to an implementation of the disclosure.

FIG. 5A is a flow diagram illustrating a method 500 for producing an orthotic device according to an implementation of the disclosure. The method 500 may be performed by processing logic that includes hardware (e.g., circuitry, dedicated logic, programmable logic, microcode, etc.), software (e.g., instructions run on a processing device to perform hardware simulation), or a combination thereof. In one implementation, method 500 may be performed by the model generation component 160 as described with respect to FIGS. 1A and 1B.

Referring to FIG. 5A, method 500 begins at block 505 when data related to a patient is received from a client device (e.g., client device 110A). The data includes patient information and/or image data representative of a body part of the patient. In one implementation the data includes IMU data (e.g., IMU data 116A). In one implementation, the body part is a foot of the patient. In one implementation, the image data is representative of a mold of a body part of the patient. In an alternative implementation, the image data is representative of an inanimate object. In one implementation, at least some of the data is received from an additional client device (such as a client device of a physician) or data store (e.g., data store 140).

At block 510, 3D model data representative of the body part is generated based on the image data. In one implementation, the 3D model data may be generated based on the image data, the patient information, and/or the IMU data. In one implementation, if the image data includes video, a plurality of frames are extracted from the video based on the IMU data. The 3D model data of the body part may be generated at least in part from the plurality of frames.

In one implementation, a unique visual pattern may be identified within a captured image or frame of the image data. The unique visual pattern may be a pattern of symbols, colors, etc., which, if recognized (e.g., by an image processing algorithm), may be used to extract depth information from the captured image or frame. Accordingly, the depth information, combined with depth information from different views of the body part, may be used to generate the 3D model data. In one implementation, the unique visual pattern is present on an article worn on the body part of the patient (e.g., a patterned sock as illustrated in FIGS. 2B and 3). In one implementation, the user device may have captured depth information (e.g., using an infrared depth sensor), which may have been received along with the image data. The depth information captured by the user device may also be used to generate the 3D model data.

At block 515, parametric CAD model data of the orthotic device is generated based on the 3D model data and the patient information. The parametric CAD model data may correspond to a 3D representation of the orthotic device. In one implementation, measurements are extracted from the 3D model data (e.g., toe, inner arch, outer arch, heel, etc.), which are used to define parameters for the parametric CAD model data. In one implementation, the parameters may define a material density profile for the orthotic device (e.g., to provide a 3D location-dependent stiffness within the orthotic device). The parametric CAD model data may define include discrete structural features that map to the density profile (e.g., which may be a continuous density profile). The structural features may include holes, apertures, internal pockets, internal bridges/trusses, etc. In one implementation, if an orthotic device is to have a stiffness gradient in a top surface that increases from a first end to a second end, the parametric CAD model may include a plurality of holes defined in the top surface, with a decreasing number of holes from the first end to the second end.

At block 520, the parametric CAD model data is transmitted to a 3D printer (e.g., 3D printer 132A). The 3D printer is to generate the orthotic device based on the parametric CAD model data. In one implementation, the parametric CAD model data is in a suitable format for 3D printing. In one implementation, the parametric CAD model data is converted into a suitable format for 3D printing prior to transmitting the parametric CAD model data to the 3D printer. In one implementation, the parametric CAD model data may define one or more layers within the orthotic device. The layers may then be printed and laminated together. In one implementation, the material of the one or more layers may include, but is not limited to, nylon, antimicrobial nylon, ABS plastic, PLA plastic, polyurethane, leather, foam, or combinations thereof. The printed orthotic device may be colored by dyeing or through chemical or photo exposure. The printed orthotic device may be covered with a material, such as leather, neoprene, a fabric, etc. In one implementation, information on user preferences (e.g., materials, colors, etc.) for the orthotic device may have been received in addition to the patient information and image data. In one implementation, identifying information is 3D printed onto or within the orthotic device. For example, a patient's name, a physician's name, a date of manufacture, a name of the manufacturing facility, a company name, etc. may be printed onto or within the orthotic device.

FIG. 5B is a flow diagram illustrating a method 550 for capturing data from a user for use in producing an orthotic device according to an implementation of the disclosure. The method 550 may be performed by processing logic that includes hardware (e.g., circuitry, dedicated logic, programmable logic, microcode, etc.), software (e.g., instructions run on a processing device to perform hardware simulation), or a combination thereof. In one implementation, method 550 may be performed by a user interface of a client device (e.g., any of user interfaces 112A-112Z of client devices 110A-110Z, respectively) as described with respect to in FIGS. 1A, 1B, 2A, and 2B.

Referring to FIG. 5B, method 550 begins at block 555 when a plurality of user inputs are received at a client device (e.g., client device 110A, which may be a mobile device). In one implementation, the client device provides an interface (e.g., user interface 112A) that prompts the user to enter patient information (e.g., height, weight, age, pre-existing medical conditions, etc.). In some implementations, the client device prompts the user for a subset of patient information (e.g., if some patient information was received previously). In some implementations, the client device does not prompt the user for patient information, and block 555 is omitted entirely.

At block 560, one or more indicators are generated at the client device to guide capturing of image data of a body part. In one implementation, the one or more indicators comprise at least one of an audio cue (e.g., audio instructions, a bell indicating successful capture, etc.), a visual cue (e.g., a targeting reticle, a shape of a foot, instructions in the form of text, etc.), or a haptic cue (e.g., a vibration indicating successful capture). In one implementation, the client device is a mobile device (e.g., such as a tablet, smartphone, etc.) equipped with a camera such that the user can view a display while capturing image data. In another implementation, a separate camera may be used to capture the image data and a separate device may provide indicators to the user. In some implementations, the user may use a camera to capture the image data without any feedback indicators (e.g., visual, audio, and haptic cues).

At block 565, the image data of the body part is captured. In one implementation, the patient may be wearing an article (e.g., a sock) having patterns from which depth information can be extracted during downstream image processing. In one implementation, after the image data is captured, block 560 and 565 may be repeated to continue capturing image data (e.g., to acquire additional views of the body part).

At block 570, the patient information and the image data are transmitted to a remote device for processing (e.g., via the network 150). The remote device (e.g., modeling server 120) is to generate, based on the patient information and the image data, a first dataset corresponding to a first 3D representation of the body part (e.g., using model generation component 160). In one implementation, at least a portion of the data is processed locally (e.g., by the client device). In one implementation, depth data may be transmitted to the remote device, the depth data having been captured by the client device during image data capture.

In one implementation, the client device may receive (e.g., from the modeling server 120) the first dataset (e.g., after the first dataset was generated by the remote device), and generate for display the first 3D representation of the body part based on the first dataset. In one implementation, the client device may receive the first dataset in response to completing a minimum number of scans sufficient for generating the first dataset. In one implementation, the client device may receive a second dataset corresponding to a second 3D representation of the orthotic device. The second dataset may be, or may be derived from, parametric CAD model data generated based on the first dataset (e.g., by the modeling server 120). The client device may receive the second dataset after the second dataset was generated by the remote device. The client device may generate for display the second 3D representation of the orthotic device. In one implementation, if additional user inputs are received at the client device (e.g., updated patient information), the client device may generate for display an updated 3D representation of the orthotic device based at least in part on the updated patient information. In one implementation, the updated information is transmitted to the remote device, which in turn generates an updated data set corresponding to the updated 3D representation of the orthotic device, and transmits the updated data set to the client device. In one implementation, the client device generates an updated dataset corresponding to the updated 3D representation of the orthotic device.

For simplicity of explanation, the methods of this disclosure are depicted and described as a series of acts. However, acts in accordance with this disclosure can occur in various orders and/or concurrently, and with other acts not presented and described herein. Furthermore, not all illustrated acts may be required to implement the methods in accordance with the disclosed subject matter. In addition, those skilled in the art will understand and appreciate that the methods could alternatively be represented as a series of interrelated states via a state diagram or events. Additionally, it should be appreciated that the methods disclosed in this specification are capable of being stored on an article of manufacture, such as a computer-readable device or storage media, to facilitate transporting and transferring such methods to computing devices. Accordingly, the term "article of manufacture", as used herein, is intended to include a computer program accessible from any computer-readable device or storage media.

Figure 6:
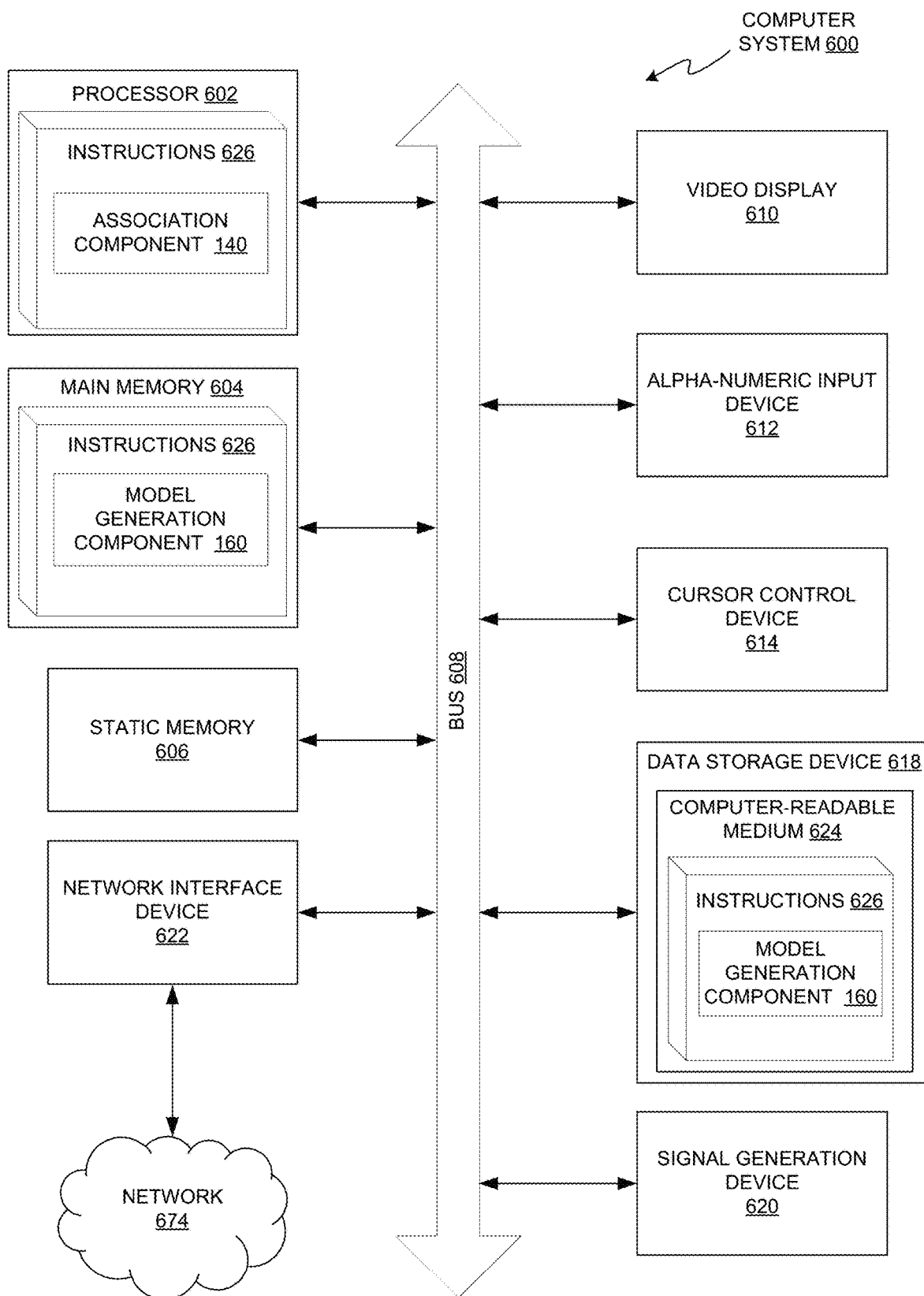
FIG. 6 is a block diagram illustrating an exemplary computer system for use in accordance an implementation of the disclosure

FIG. 6 illustrates a diagrammatic representation of a machine in the exemplary form of a computer system 600 within which a set of instructions, for causing the machine to perform any one or more of the methodologies discussed herein, may be executed. In alternative implementations, the machine may be connected (e.g., networked) to other machines in a LAN, an intranet, an extranet, or the Internet. The machine may operate in the capacity of a server or a client machine in client-server network environment, or as a peer machine in a peer-to-peer (or distributed) network environment. The machine may be a personal computer (PC), a tablet PC, a set-top box (STB), a Personal Digital Assistant (PDA), a cellular telephone, a web appliance, a server, a network router, switch or bridge, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein. Some or all of the components of the computer system 600 may be utilized by or illustrative of any of client devices 110A-110Z, modeling server 120, production server 130, 3D printers 132A-132Z, and data store 140.

The exemplary computer system 600 includes a processing device (processor) 602, a main memory 604 (e.g., read-only memory (ROM), flash memory, dynamic random access memory (DRAM) such as synchronous DRAM (SDRAM) or Rambus DRAM (RDRAM), etc.), a static memory 606 (e.g., flash memory, static random access memory (SRAM), etc.), and a data storage device 618, which communicate with each other via a bus 608.

Processor 602 represents one or more general-purpose processing devices such as a microprocessor, central processing unit, or the like. More particularly, the processor 602 may be a complex instruction set computing (CISC) microprocessor, reduced instruction set computing (RISC) microprocessor, very long instruction word (VLIW) microprocessor, or a processor implementing other instruction sets or processors implementing a combination of instruction sets. The processor 602 may also be one or more special-purpose processing devices such as an application specific integrated circuit (ASIC), a field programmable gate array (FPGA), a digital signal processor (DSP), network processor, or the like. The processor 602 is configured to execute instructions 626 for performing the operations and steps discussed herein.

The computer system 600 may further include a network interface device 622. The computer system 600 also may include a video display unit 610 (e.g., a liquid crystal display (LCD), a cathode ray tube (CRT), or a touch screen), an alphanumeric input device 612 (e.g., a keyboard), a cursor control device 614 (e.g., a mouse), and a signal generation device 620 (e.g., a speaker). In some implementations, the signal generation device 620 may include a vibrational actuator (e.g., for providing haptic feedback).

The data storage device 618 may include a computer-readable storage medium 624 on which is stored one or more sets of instructions 626 (e.g., software) embodying any one or more of the methodologies or functions described herein. The instructions 626 may also reside, completely or at least partially, within the main memory 604 and/or within the processor 602 during execution thereof by the computer system 600, the main memory 604 and the processor 602 also constituting computer-readable storage media. The instructions 626 may further be transmitted or received over a network 674 (e.g., the network 150) via the network interface device 622.

In one implementation, the instructions 626 include instructions for one or more model generation components 160, which may correspond to the identically-named counterpart described with respect to FIGS. 1A and 1B. While the computer-readable storage medium 624 is shown in an exemplary implementation to be a single medium, the terms "computer-readable storage medium" or "machine-readable storage medium" should be taken to include a single medium or multiple media (e.g., a centralized or distributed database, and/or associated caches and servers) that store the one or more sets of instructions. The terms "computer-readable storage medium" or "machine-readable storage medium" shall also be taken to include any transitory or non-transitory medium that is capable of storing, encoding or carrying a set of instructions for execution by the machine and that cause the machine to perform any one or more of the methodologies of the present disclosure. The terms "computer-readable storage medium" or "machine-readable storage medium" shall accordingly be taken to include, but not be limited to, solid-state memories, optical media, and magnetic media.

In the foregoing description, numerous details are set forth. It will be apparent, however, to one of ordinary skill in the art having the benefit of this disclosure, that the present disclosure may be practiced without these specific details. In some instances, well-known structures and devices are shown in block diagram form, rather than in detail, in order to avoid obscuring the present disclosure.

Some portions of the detailed description may have been presented in terms of algorithms and symbolic representations of operations on data bits within a computer memory. These algorithmic descriptions and representations are the means used by those skilled in the data processing arts to most effectively convey the substance of their work to others skilled in the art. An algorithm is herein, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the foregoing discussion, it is appreciated that throughout the description, discussions utilizing terms such as "sending", "receiving", "transmitting", "forwarding", "caching", "causing", "providing", "generating", "adding", "subtracting", "removing", "analyzing", "determining", "enabling", "identifying", "modifying" or the like, refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such information storage, transmission or display devices.

The disclosure also relates to an apparatus, device, or system for performing the operations herein. This apparatus, device, or system may be specially constructed for the required purposes, or it may include a general purpose computer selectively activated or reconfigured by a computer program stored in the computer. Such a computer program may be stored in a computer- or machine-readable storage medium, such as, but not limited to, any type of disk including floppy disks, optical disks, compact disk read-only memories (CD-ROMs), and magnetic-optical disks, read-only memories (ROMs), random access memories (RAMs), EPROMs, EEPROMs, magnetic or optical cards, or any type of media suitable for storing electronic instructions.

The words "example" or "exemplary" are used herein to mean serving as an example, instance, or illustration. Any aspect or design described herein as "example" or "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or". That is, unless specified otherwise, or clear from context, "X includes A or B" is intended to mean any of the natural inclusive permutations. That is, if X includes A; X includes B; or X includes both A and B, then "X includes A or B" is satisfied under any of the foregoing instances. In addition, the articles "a" and "an" as used in this application and the appended claims should generally be construed to mean "one or more" unless specified otherwise or clear from context to be directed to a singular form. Reference throughout this specification to "an implementation" or "one implementation" means that a particular feature, structure, or characteristic described in connection with the implementation is included in at least one implementation. Thus, the appearances of the phrase "an implementation" or "one implementation" in various places throughout this specification are not necessarily all referring to the same implementation. Moreover, it is noted that the "A-Z" notation used in reference to certain elements of the drawings is not intended to be limiting to a particular number of elements. Thus, "A-Z" is to be construed as having one or more of the element present in a particular implementation.

It is to be understood that the above description is intended to be illustrative, and not restrictive. Many other implementations will be apparent to those of skill in the art upon reading and understanding the above description. The scope of the disclosure should, therefore, be determined with reference to the appended claims, along with the full scope of equivalents to which such claims are entitled.

What is claimed is:

1. A method of characterizing a foot of an individual, the method comprising:
   causing a display device of a mobile device to display live video captured by a camera of the mobile device;
   causing the display device to display one or more visual indicators overlaid on the live video to guide image capture of the foot in different orientations;
   capturing, by the camera, a plurality of images of the foot in the different orientations, wherein a visual appearance of the one or more visual indicators is adjusted to facilitate capture of the plurality of images in the different orientations;
   computing, or transmitting the plurality of images to a server for computing, a data set corresponding to a three-dimensional representation of the foot, the data set to be computed at least partially from the plurality of images of the foot in the different orientations, wherein the three-dimensional representation of the foot can be inspected, re-used, or re-processed based on new algorithms and/or updated data for the individual; and
   causing the display device to display information or data relevant to the foot or associated with the three-dimensional representation of the foot.

2. The method of claim 1, further comprising:
   generating, by the mobile device, a haptic cue along with the one or more visual indicators.

3. The method of claim 1, further comprising:
   receiving a plurality of user inputs, the user inputs corresponding to physical parameters of the individual, wherein a plurality of physical dimensions of the foot are computed based at least partially on the physical parameters.

4. The method of claim 3, further comprising:
   capturing depth data with respect to the foot, wherein the plurality of physical dimensions of the foot are computed based at least partially on the depth data.

5. The method of claim 1, wherein the server is to generate model data representative of an orthotic device based at least partially on a plurality of physical dimensions of the foot and the three-dimensional representation of the foot to facilitate optimization of mechanical properties of the orthotic device to the individual.

6. The method of claim 5, wherein the server is to transmit the model data to a fabrication device, wherein the fabrication device is to fabricate the orthotic device based on the model data.

7. The method of claim 1, further comprising:
   determining that the foot is in a target orientation during image capture based at least partially on inertial measurement data received while video of the foot is captured.

8. A system for characterizing a foot of an individual, the system comprising:
   a display device;
   a camera; and
   a processing device of a mobile device operatively coupled to the camera and the display device, wherein the processing device is configured to:
   cause the display device to display live video captured by the camera;
   cause the display device to display one or more visual indicators overlaid on the live video to guide image capture of the foot in different orientations;
   cause the camera to capture a plurality of images of the foot in the different orientations, wherein a visual appearance of the one or more visual indicators is adjusted to facilitate capture of the plurality of images in the different orientations;
   compute, or transmit the plurality of images to a server for computing, a data set corresponding to a three-dimensional representation of the foot, the data set to be computed at least partially from the plurality of images of the foot in the different orientations, wherein the three-dimensional representation of the foot can be inspected, re-used, or re-processed based on new algorithms and/or updated data for the individual; and
   cause the display device to display information or data relevant to the foot or associated with the three-dimensional representation of the foot.

9. The system of claim 8, wherein the processing device is further configured to:
   cause the mobile device to generate a haptic cue along with the one or more visual indicators.

10. The system of claim 8, wherein the processing device is further configured to:

receive a plurality of user inputs, the user inputs corresponding to physical parameters of the individual, wherein a plurality of physical dimensions of the foot are computed based at least partially on the physical parameters.

11. The system of claim 10, wherein the processing device is further configured to:
cause the mobile device to capture depth data with respect to the foot, wherein the plurality of physical dimensions of the foot are computed based at least partially on the depth data.

12. The system of claim 8, wherein the server is to generate model data representative of an orthotic device based at least partially on a plurality of physical dimensions of the foot and the three-dimensional representation of the foot to facilitate optimization of mechanical properties of the orthotic device to the individual.

13. The system of claim 12, wherein the server is to transmit the model data to a fabrication device, wherein the fabrication device is to fabricate the orthotic device based on the model data.

14. The system of claim 8, wherein the processing device is further configured to:
determine that the foot is in a target orientation during image capture based at least partially on inertial measurement data received while video of the foot is captured.

15. A non-transitory computer-readable medium having instructions encoded thereon that, when executed by a processing device of a mobile device, cause the processing device to:
cause a display device of the mobile device to display live video captured by a camera;
cause the display device to display one or more visual indicators overlaid on the live video to guide image capture of a foot of an individual in different orientations;
cause the camera to capture a plurality of images of the foot in the different orientations, wherein a visual appearance of the one or more visual indicators is adjusted to facilitate capture of the plurality of images in the different orientations;
compute, or transmit the plurality of images to a server for computing, a data set corresponding to a three-dimensional representation of the foot, the data set to be computed at least partially from the plurality of images of the foot in the different orientations, wherein the three-dimensional representation of the foot can be inspected, re-used, or re-processed based on new algorithms and/or updated data for the individual; and
cause the display device to display information or data relevant to the foot or associated with the three-dimensional representation of the foot.

16. The non-transitory computer-readable medium of claim 15, wherein the instructions further cause the processing device to:
cause the mobile device to generate a haptic cue along with the one or more visual indicators.

17. The non-transitory computer-readable medium of claim 15, wherein the instructions further cause the processing device to:
receive a plurality of user inputs, the user inputs corresponding to physical parameters of the individual, wherein a plurality of physical dimensions of the foot are computed based at least partially on the physical parameters.

18. The non-transitory computer-readable medium of claim 17, wherein the instructions further cause the processing device to:
cause the mobile device to capture depth data with respect to the foot, wherein the plurality of physical dimensions of the foot are computed based at least partially on the depth data.

19. The non-transitory computer-readable medium of claim 15, wherein the server is to generate model data representative of an orthotic device based at least partially on a plurality of physical dimensions of the foot and the three-dimensional representation of the foot to facilitate optimization of mechanical properties of the orthotic device to the individual, and wherein the server is to transmit the model data to a fabrication device, wherein the fabrication device is to fabricate the orthotic device based on the model data.

20. The non-transitory computer-readable medium of claim 15, wherein the instructions further cause the processing device to:
determine that the foot is in a target orientation during image capture based at least partially on inertial measurement data received while video of the foot is captured.

* * * * *